United States Patent [19]

Ewing

[11] Patent Number: 4,677,932
[45] Date of Patent: Jul. 7, 1987

[54] HANDICAP TURN SIGNAL BAR FOR AN AUTOMOBILE

[76] Inventor: Joseph Ewing, 8245 Peach Orchard Rd., Baltimore, Md. 21222

[21] Appl. No.: 844,185

[22] Filed: Mar. 26, 1986

[51] Int. Cl.⁴ .......................... H01H 3/16; H01H 9/00
[52] U.S. Cl. ..................................... 116/35 R; 74/523; 200/61.27; 200/61.54
[58] Field of Search ............. 116/28 R, 35 R; 74/491, 74/494, 523; 200/61.27, 61.54; 340/22, 74, 76, 138, 140

[56] References Cited

U.S. PATENT DOCUMENTS

| | | | |
|---|---|---|---|
| 3,226,997 | 1/1966 | Malloy | 74/491 |
| 3,576,530 | 4/1971 | Buechler et al. | 340/74 |
| 4,218,595 | 8/1980 | Honjo | 200/61.54 |
| 4,293,743 | 10/1981 | Iwata et al. | 200/61.27 |
| 4,423,297 | 12/1983 | Berginski | 200/61.54 |

*Primary Examiner*—Richard R. Stearns
*Attorney, Agent, or Firm*—John Cyril Malloy

[57] ABSTRACT

A handicap turn signal bar is adapted to be mounted on an automobile's steering column. The steering column has a vertically actuated turn signal lever horizontally positioned and extending generally radially from the steering column. The handicap turn signal bar includes an elongated lever member substantially parallel to the turn signal lever. The member is pivotally mounted at the bottom of the steering column and one longitudinal end of the member is proximate a portion of the steering wheel. The other longitudinal end of the member is disposed in the vertical plane movement of the turn signal lever. A split clamp is attached to that other end of the member and is removably attached to the turn signal lever. The split clamp includes first and second mating parts which define a varied dimensional through-hole adapted to loosely encircle the turn signal lever. Due to the loose encirclement of the lever, rotational controls at the extensive end of the lever are still operable even though the split clamp is attached to the turn signal lever.

4 Claims, 6 Drawing Figures

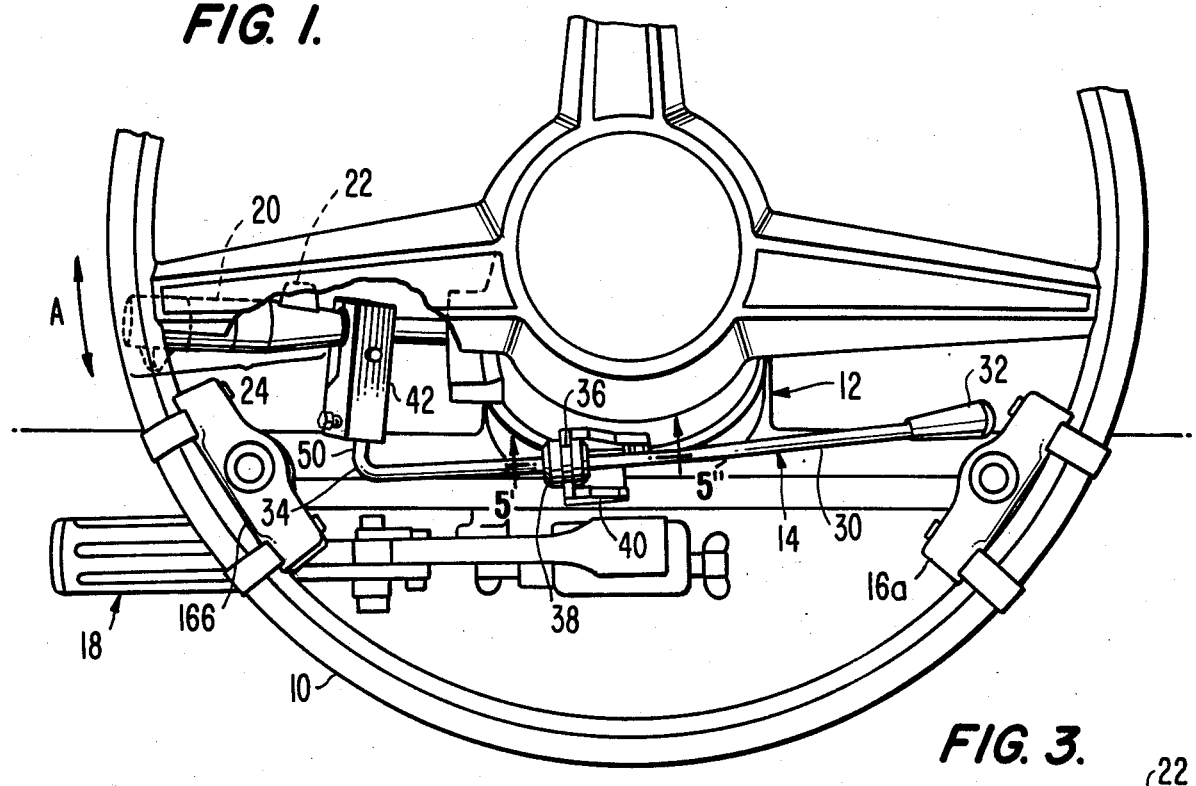
FIG. 1.
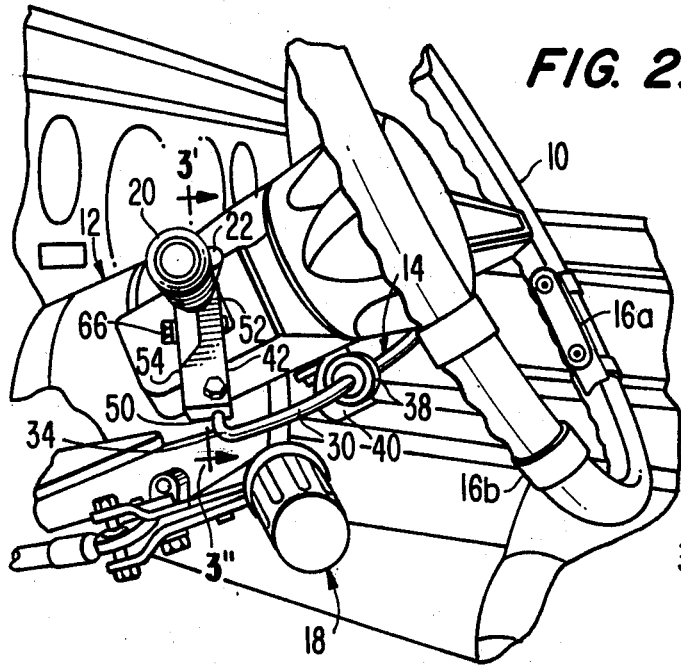
FIG. 2.
FIG. 3.
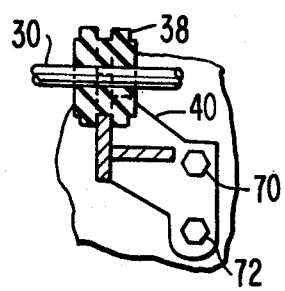
FIG. 5.
FIG. 4.
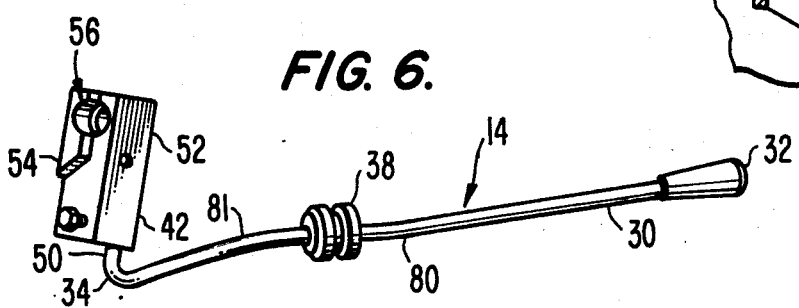
FIG. 6.

HANDICAP TURN SIGNAL BAR FOR AN AUTOMOBILE

BACKGROUND OF THE INVENTION

This invention relates to a handicap turn signal bar and particularly relates to a turn signal bar that converts a left-handed vertically actuated turn signal control lever into a right-handed turn signal control without significantly inhibiting actuation of the rotational accessory controls mounted in the left-handed turn signal lever.

In many automobiles, the turn signal controls consist of a turn signal lever extending radially from the steering column. The lever is vertically actuated in order to control the left hand and right hand turn signal lights. In order to convert a conventional automobile into an automobile which can be controlled by a paraplegic handicapped person, the foot controls in the conventional automobile are converted to hand controls. For example, the footpedal throttle is coupled to a throttle control rod that extends substantially parallel to the steering column of the car and terminates in a throttle and brake hand control mechanism. The foot brake pedal is also coupled to a brake control rod which extends to the throttle and brake hand control. By leveraged movement of a hand grip, the driver actuates the throttle foot pedal vis-a-vis the throttle control rod. By pushing the hand grip laterally downward parallel to the steering column, the driver brakes the automobile vis-a-vis the brake control rod. This throttle and brake hand control requires almost the continuous use of the left hand of the driver. Therefore, the driver has considerable difficulty in operating the left-handed turn signal lever on a conventional automobile unless he releases the throttle and brake hand control. This release of the brake and throttle hand control is unacceptable in many driving situations.

In order to make the left-handed turn signal lever control accessible to the right hand of a driver, a prior art device was devised that included a vertically oriented arm extending upward from the left-handed turn signal lever. One end of the arm was positioned proximate a portion of the steering wheel such that the right hand of the driver could steer the vehicle and actuate the turn signal lever via the vertical arm. The other end of the vertical arm terminated in a block having a hole therein through which extended the lever. To attach the prior art turn signal bar to the turn signal lever of the automobile, all the radially extensive mechanisms on the turn signal lever had to be removed such that the block could be slipped over the extensive end of the turn signal lever. A set screw extended into the hole of the block and frictionally engaged the lever to fix the vertical arm onto the turn signal lever.

When automobile manufacturers added additional controls for other accessories onto the extensive end of the turn signal lever, removal of those controls was not possible and the prior art turn signal became inoperable. These accessory controls include wiper controls which rotate about the longitudinal axis of the turn signal lever. The rotational movement from the wiper control knob is carried by a control rod to a complementary mechanism in the steering column. The prior art turn signal bar would not permit use of this accessory control notwithstanding the inability of the block of the bar to fit over the accessory control knob.

OBJECTS AND SUMMARY OF THE INVENTION

It is an object of the present invention to provide a handicapped turn signal device for converting a left-handed turn signal lever control to a right-handed turn signal control.

It is another object of the invention to provide a turn signal bar which permits use of the rotationally actuated accessory controls, disposed at the extensive end of the turn signal lever, notwithstanding the attachment of the turn signal bar to the lever.

In summary, one embodiment of the handicap turn signal bar includes a elongated lever member substantially parallelly disposed with respect to the turn signal lever and pivotably mounted on the steering column of the automobile. One longitudinal end of the lever member, when the member is so mounted, is proximate a portion of the steering wheel such that the right hand of the driver can actuate the turn signal bar. The other longitudinal end of the lever member is disposed in the vertical plane of movement of the turn signal lever. A split clamp is attached to that other longitudinal end. The split clamp includes first and second mating parts that define a varied dimensional through hole through which is disposed the turn signal lever. The through-hole in one embodiment has two large diameter partial bores open to opposing faces of the split clamp and a smaller bore hole extending therebetween. The through-hole is defined by the first and second mating parts such that the first mating part is removeably attachable to the second mating part and the split clamp is attachable and detachable from the turn signal lever. The through-hole has a cross sectional area larger than the area of the adjacent portion of the turn signal lever to permit multiple movements of the turn signal lever.

BRIEF DESCRIPTION OF THE DRAWINGS

The subject matter which is regarded as the invention is particularly pointed out and distinctly claimed in the concluding portion of the specification. The invention, however, together with further objects and advantages thereof, may best be understood by reference to the following description taken in conjunction with the accompanying drawings in which:

FIG. 1 illustrates a front view of a steering wheel, steering column and the attached handicapped turn signal bar in accordance with the principles of the present invention;

FIG. 2 illustrates the side view of the wheel, steering column and attached handicapped turn signal bar;

FIG. 3 is a cross-sectional view from the perspective of section line 3'—3" in FIG. 2;

FIG. 4 is a cross-sectional view of the split clamp from the perspective of section line 4'—4" in FIG. 3;

FIG. 5 illustrates a partial bottom view of the mounting bracket and rubber grommet holding the turn signal bar from the perspective of section Line 5'—5" in FIG. 1; and, FIG. 6 illustrates a perspective view of a freestanding turn signal bar.

DETAILED DESCRIPTION OF THE DRAWINGS

The present invention relates to a handicap turn signal bar and particularly relates to a bar which converts a left-handed turn signal control into a right-handed turn signal control and permits actuation of the rotatable control accessory knobs at the extensive end of the left-handed turn signal lever.

FIG. 1 illustrates a front view of steering wheel 10 attached to one end of steering column 12. FIG. 2 illustrates the side view thereof. Handicap turn signal bar 14 is attached to the lower region of steering column 12 in both FIGS. 1 and 2. It is to be noted that turn signal bar could be attached to the upper region of steering column 12 rather than the lower region. Steering wheel 10 includes brackets 16a and 16b which are adapted to hold knobs enabling the driver to better steer the automobile. Throttle and brake hand control mechanism 18 is partially illustrated. Extending radially from steering column 12 is turn signal lever 20. Turn signal lever 20 is vertically actuated (Arrow A) to signal left and right hand turns of the vehicle. Lever 20 includes wiper control knob 22 which is part of the rotatable accessory control mechanism 24 at the radially extensive end of lever 20. In this illustrated embodiment, a 1985 Pontiac Grand Prix automobile is used in conjunction with the invention.

Handicap turn signal bar 14 includes an elongated lever member 30 having one longitudinal end 32 and a second longitudinal end 34. End 32 is proximate a portion of the steering wheel 10 in order to allow the right hand of the driver to actuate turn signal bar 14. In a preferred embodiment, end 32 is approximately 3 inches from the adjacent region of steering wheel 10. Elongated lever member 30 is pivotally mounted at pivot point 36 on steering column 12 via rubber grommet 38 and mounting bracket 40.

Longitudinal end 34 is disposed in the substantially vertical plane of movement of turn signal lever 20 as best shown in FIG. 2 along section line 3'—3". It is to be understood that the terms "vertical", "horizontal" and "radial" only designate general relationships of the components. For example, turn signal lever 20 may be vertically actuated along section line 3'—3" or that lever can be actuated along a line 10 degrees radially offset from section line 3'-3". In other words, the term vertical is used to encompass all reasonably vertical movements. Also, the term "horizontal" is meant to encompass all generally horizontal positions. Longitudinal end 34 is disposed in the vertical plane of movement of turn signal lever 20. Turn signal bar 14 includes, in this embodiment, a vertically extensive portion 50 which extends into split clamp 42. Split clamp 42 includes mating part 52 and mating part 54. Both mating parts define a varied dimensional through-hole, through which is disposed turn signal lever 20.

FIG. 3 is a cross-sectional view of split clamp 42 from the perspective of section line 3'—3" in FIG. 2. The section line travels along one mating face of part 54. Varied dimensional through-hole 56 includes a large diameter partial bore 58, another large diameter partial bore 59, and a smaller bore hole 60 therebetween. Small bore hole is defined by an intermediate lip. Bores 58 and 59 are open to opposing faces of split clamp 42. As shown in FIG. 3, rotatable wiper control 22 is in close proximity to the opening of large diameter partial bore 58. Wiper control 22 is affixed to control rod 62 which rotates with respect to the axis of lever 20 about core rod 64. Returning to FIG. 2, parts 52 and 54 are removably attached to each other by threaded bolt 66 which mates with female threads in hole 68.

As best illustrated in FIG. 3, varied dimensional through-hole 56 has a cross-sectional area larger than an area of the adjacent portion of the turn signal lever to permit multiple movements of the turn signal lever therein. Since the driver actuates turn signal bar 14 by vertically moving end 32 (see FIG. 1) and since pivot point 36 may not be precisely aligned with the pivotal point of turn signal lever 20, the vertical movement of split clamp 42 most likely will not match the vertical movement of all the adjacent portions of lever 20, that is the lever moves in a vertical sense within through bore 56. This is one of the multiple movements permitted by the loose encirclement of the turn signal lever by the through-hole. Another movement permitted by through-hole 56 is the rotational movement of wiper control 22 and control rod 62. It is to be noted that through-hole 56 may have multiple diameters throughout rather than two distinct diameters.

FIG. 4 is a cross-sectional view of split clamp 42 from the perspective of section line 4'—4" in FIG. 3. In FIG. 4, mating part 54 is securely fixed via threaded bolt 66 to part 52. As for the varied dimensional through-hole in a preferred embodiment, larger partial bore 58 is $\frac{5}{8}$ inches in diameter and smaller bore hole 60 is $\frac{1}{2}$ inches in diameter. The longitudinal dimension of split clamp 42 is perferrably 2.5 inches and end 50 of the elongated member fits into a quarter inch diameter hole extending $\frac{3}{4}$ inches into the lower end of split clamp 42. Threaded set bolt 65, best illustrated in FIG. 3, secures end 50 into split clamp 42. Split clamp 42 includes $\frac{1}{4}$ inch fine female threads in a bore which mates with the threads on set bolt 65.

FIG. 5 illustrates a bottom view from the perspective of section line 5'—5" in FIG. 1. Mounting bracket 40 and rubber grommet 38 are shown retaining elongated member 30. Bracket 40 is bolted to steering column 12 via bolts 70 and 72. It is to be noted that a further bracket encompassing the circumference of rubber grommet 38 may be included as part of this device.

FIG. 6 shows a perspective view of freestanding turn signal bar 14. As noted by comparing FIGS. 1, 2 and 6, elongated member 30 has a slight bend at point 80 which brings end 32 closer to steering wheel 10. Another bend at point 81 brings end 34 in the vertical plane of movement of turn signal lever 20. The positioning and degree of these bends depends upon the positional relationship between turn signal lever 20 and steering wheel 10.

The claims appended hereto are meant to cover all modifications within the true spirit and scope of this invention.

What I claim is:

1. A handicap turn signal bar adapted to be mounted on an automobile's steering column, said steering column terminating in a steering wheel and having a vertically actuated turn signal lever substantially horizontally positioned and extending generally radially from said steering column comprising:

an elongated lever member substantially parallelly disposed with respect to said turn signal lever and pivotably mounted on said steering column, one longitudinal end of said member adapted to be proximate a portion of said steering wheel and the other longitudinal end of said member disposed in the vertical plane of movement of said turn signal lever;

a split clamp attached to said other longitudinal end of said member and having first and second mating parts that define a varied dimensional through-hole adapted to loosely encircle said turn signal lever, said first mating part being removably attached to said second mating part such that said split clamp is adapted to be detachable from said turn signal lever; and, wherein said vertical dimensional through-hole has a cross-sectional area larger than the area of the adjacent portion of said turn signal lever to permit multiple movements of said turn signal lever therein.

2. A handicap turn signal bar as claimed in claim 1 wherein said turn signal lever includes a rotatable accessory control rod longitudinally disposed to cover at least said adjacent portion of said turn signal lever, said varied dimensional through-hole having sufficient clearance with said control rod to permit rotational movement thereof as one of said multiple movements.

3. A handicap turn signal bar as claimed in claim 2 wherein said varied dimensional through-hole comprises two large diameter partial bores open to opposing faces of said split clamp and a smaller bore hole extending therebetween defined by an intermediate lip in said split clamp.

4. A handicap turn signal bar as claimed in claim 3 including a mounting bracket affixed to said steering column and retaining a rubber grommet defining the pivot point of said member.

* * * * *